United States Patent [19]

Negersmith

[11] 4,300,906

[45] Nov. 17, 1981

[54] METHOD FOR THE OPERATION OF AUTOMATED ANALYSIS APPARATUS

[75] Inventor: Kent M. Negersmith, Carmel, N.Y.

[73] Assignee: Technicon Instruments Corp., Tarrytown, N.Y.

[21] Appl. No.: 194,320

[22] Filed: Oct. 6, 1980

[51] Int. Cl.³ .............................................. G01N 35/08
[52] U.S. Cl. ................................ 23/230 A; 23/230 R; 422/81; 422/82
[58] Field of Search ......................... 23/230 R, 230 A; 422/81, 82

[56] References Cited

U.S. PATENT DOCUMENTS

| | | | |
|---|---|---|---|
| 3,600,953 | 8/1971 | Isreeli et al. | 422/82 X |
| 4,224,033 | 9/1980 | Hansen et al. | 422/82 X |
| 4,253,846 | 3/1981 | Smythe et al. | 23/230 R |

Primary Examiner—Ronald Serwin
Attorney, Agent, or Firm—S. P. Tedesco

[57] ABSTRACT

Method is provided for the operation of substantially constant flow rate sample analysis apparatus in such manner that the adverse effects upon sample analysis accuracy of periodic variations in analysis apparatus flow rate and/or sample-analysis reagent proportioning are negated to insure the sample-to-sample consistency and accuracy of the sample analysis results.

11 Claims, 4 Drawing Figures

4,300,906

METHOD FOR THE OPERATION OF AUTOMATED ANALYSIS APPARATUS

BACKGROUND OF THE INVENTION

1. Field of the Invention

This invention relates to new and improved method for operating continuous-flow sample analysis apparatus.

2. Description of the Prior Art

Although a variety of automated sample analysis apparatus, for example, as disclosed in U.S. Pat. No. 3,241,432, assigned to a common assignee, operates satisfactorily to automatically react and analyze successive samples on a continuous-flow basis, unwanted variations in flow rate can and do occur which adversely affect the accuracy of the analysis. For example, such apparatus operates to detect or "view" each of a succession of reacted samples for the same predetermined period of time. It will be clear that any variations in the respective flow rates (volumes) of the successive reacted samples or in sample-reagent proportioning, as may be caused by certain faulty operations of the pumping structures of the apparatus, are reflected in the reacted sample quantity which is "viewed" or analyzed and will, of necessity, adversely affect the accuracy of the analysis results. Despite the above, no method is believed currently known for compensating and negating such adverse effects, so as to obtain overall accuracy and reliability of the analysis results.

OBJECTS OF THE INVENTION

An object of this invention is to provide a new and improved method for operating continuous-flow apparatus, so as to compensate for adverse effects due to variations in the apparatus flow rate.

Another object of this invention is to provide new and improved method for operating automated, continuous-flow and substantially constant flow rate sample analysis apparatus so as to obtain accurate and reliable analytical results, despite variations in the apparatus flow rate.

Another object of this invention is to obtain the aforesaid object without any substantial change in the configuration of such analysis apparatus or in the basic manner of operation thereof.

A further object of this invention is the provision of method, as above, which may be readily and conveniently utilized with a varity of apparatus.

SUMMARY OF THE DISCLOSURE

As disclosed herein, the new and improved method for operating automated, continuous-flow sample analysis apparatus comprises fixing the relationship between the apparatus sample detecting or "viewing" time and the operational cycle time(s) of the apparatus pump(s), so as to negate the effects of any variations in apparatus flow rate, as normally introduced into such apparatus or as caused by less than perfect performance of the apparatus pump(s). Such negation results since any such effects are applied equally to each of the samples and with appropriate apparatus calibration, consistency and accuracy of the analysis results is achieved. In one example, the "viewing" time and the operational cycle time of the apparatus pump are made equal. In another example, wherein the analysis apparatus includes multiple pumps, the operational cycle times of individual pumps are particularly related to each other and to the "viewing" time.

DESCRIPTION OF THE DRAWINGS

The above and other objects and significant advantages of this invention are believed made clear by the following detailed description thereof taken in conjunction with the accompanying drawings wherein.

DETAILED DESCRIPTION OF THE INVENTION

Figure 1:
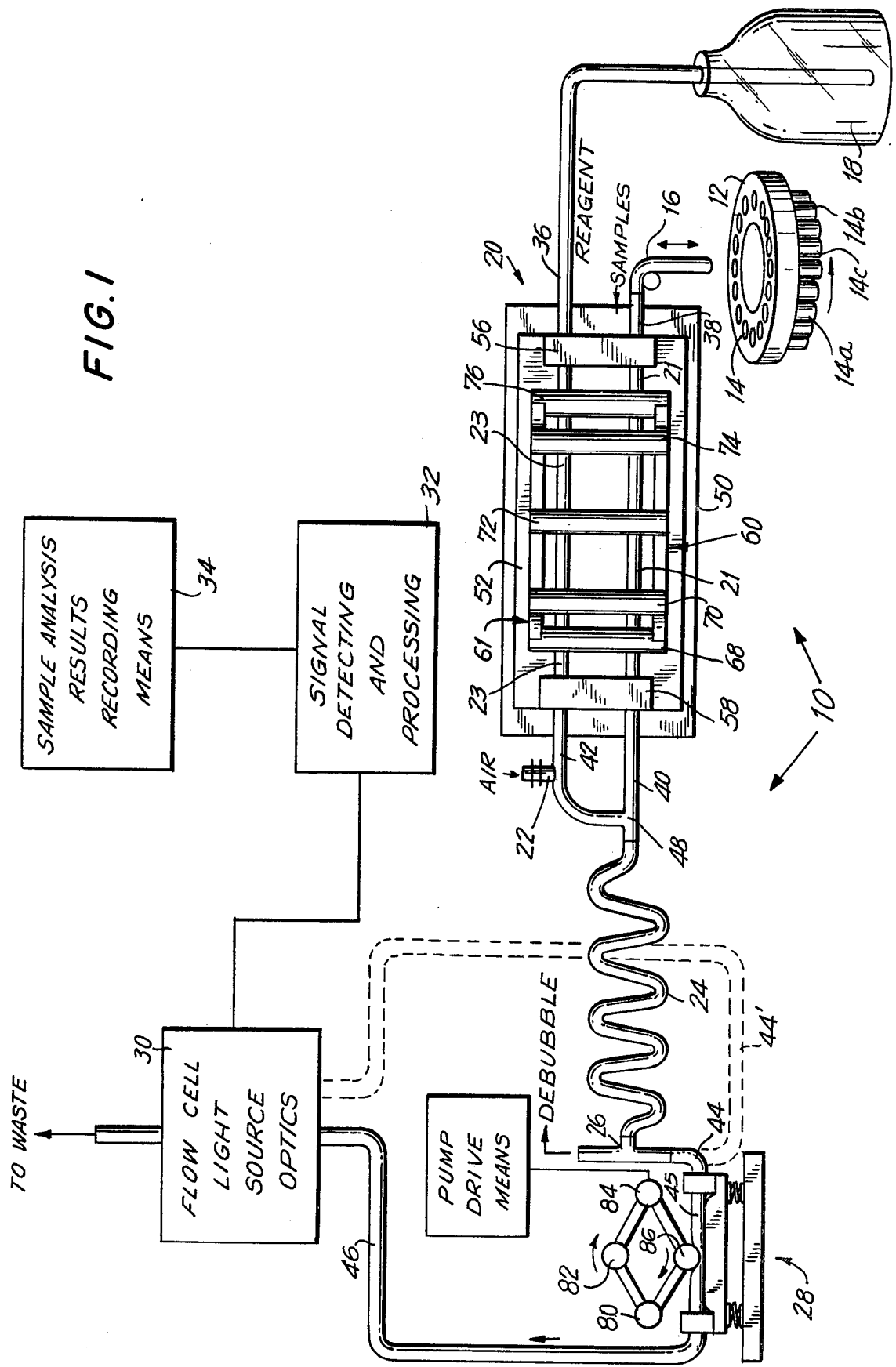
FIG. 1 is a partially schematic flow diagram of representative automated sample analysis apparatus for illustration of the application of the method of the invention thereto.

Referring to FIG. 1, a representative automated, continuous-flow sample analysis apparatus is depicted, in somewhat simplified and schematic form, and indicated generally at 10. As illustrated, the apparatus comprises an indexable turntable 12 which supports a generally circular array of spaced sample cups 14, a sample off-take or aspirating probe 16, a reagent supply 18, a main proportioning pump 20, an air bar 22, a mixing coil 24, a de-bubbler 26, a flow cell pump 28, a flow cell with attendant light source and optics as at 30, signal detecting and processing means as at 32, and analysis results recording means as at 34. Appropriate fluid conduits, as indicated at 36, 38, 40, 42, 44 and 46, respectively, are provided to connect the apparatus components, as shown.

Apparatus 10 may be adapted, for example, for the automated counting, on a continuous-flow basis, of red or white blood cells in a plurality of different blood samples contained in sample cups 14. Pumps 20 and 28 operate to pump fluids at substantially constant flow rates, in the indicated directions. As each sample cup 14 is indexed in turn by operation of turntable 12 into position beneath off-take probe 16, the latter aspirates a predetermined sample quantity therefrom for supply through conduit 36 for pumping along resilient pump tube 21, as hereafter described, and through conduit 40. Concomitantly, predetermined quantities of reagent e.g., for reacting the sample for cell counting or for analysis of a particular analyte, as known, are supplied through conduit 38 for pumping along resilient pump tube 23 and through conduit 42. The reagent stream is segmented by the periodic introduction of air segments by the action of air bar 22. The operation of air bar 22 is more particularly described in U.S. Pat. No. 3,306,229, assigned to a common assignee. The presence of such periodic air segments tends to achieve uniform proportional mixing of the sample and reagent, as particularly described in such U.S. Pat. No. 3,306,229, when mixed beyond conduit junction 48. Also, a larger air segment is aspirated along probe 16 intermediate successive sample aspirations, so as to inhibit carryover and cross-contamination between successive samples, both along conduit 38, pump tube 21 and conduit 40 and, also, subsequent to the merger of the sample and reagent streams at conduit junction 48. If desired, and to positively avoid sample carryover, a wash liquid segment can be aspirated along probe 16 and between successive sample segments, by providing a wash liquid reservoir, not shown, adjacent turntable 12 and adapting the movement of probe 16 for immersion therein, as shown in U.S. Pat. No. 3,134,263, assigned to a common assignee. Under normal operation, an air-segmented stream of precisely-proportioned, combined sample and reagent segments is directed from junction 48 and into mixing coil 24. The air segments introduced by the action of air bar 22 serve to segment the individual combined sample and reagent segments and accelerate mixing of the sample and reagent during passage through the apparatus and, particularly, through mixing coil 24.

Following mixing of the sample and reagent segments in mixing coil 24, the air-segmented reacted-sample stream, for example, reacted for cell counting, is flowed through de-bubbler 26 which removes the air segments from the steam. The "debubbled" stream is passed therefrom and through conduit 44 into resilient pump tube 45 of flow cell pump 28. Pump 28 operates to pass the debubbled stream through flow cell 30 for blood cell detection and counting, the output cell count for each successive sample being directed to signal detecting and processing means 32 for processing. The processed cell count signals are recorded by analysis results recording means 34. A more detailed understanding of automated, continuous-flow sample analysis apparatus of the nature herein discussed may be had by reference to U.S. Pat. No. 3,241,432, supra, and numerous other references known and easily available to the art.

Of particular importance is the fact that the counting of cells by apparatus 10 is effected by counting the number of cells contained in each of the successive reacted samples passing through flow cell 30 during a same predetermined time period, or interval. Thus, any condition which introduces any variation in the composition, i.e., proportioning of the sample and reagent, or in the flow rate of a reacted sample during such time interval will, of necessity, result in inaccurate results. For example, if the sample volume/reagent volume ratio of any reacted sample flowed through flow cell 30 varies, for any reason, the consistency and, accordingly, accuracy of the cell counting procedure will be lost. Also, as cell counting is a "volume" measurement, any variation in flow rate during such predetermined time interval will affect the total count.

Apparatus 10 is carefully configured to operate at a substantially constant flow rate to insure that a same quantity of each of the samples under analysis is mixed with a same volume of reagent and each reacted sample flows through the flow cell 30 at a same flow rate during the period of cell counting time. It will be readily understood that, under certain conditions, variations in such volumes and such flow rate can occur due to the inherent design or, in many instances, due to less than perfect performance by either or both of pumps 20 and 28.

Figure 2:
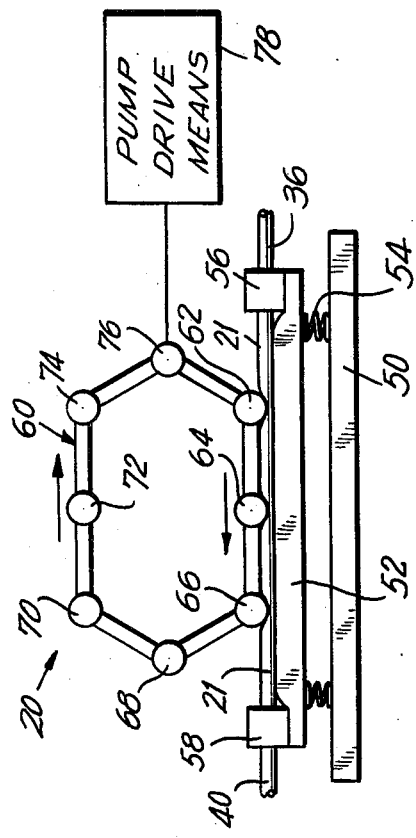
FIG. 2 is a partially schematic side view of the main apparatus proportioning pump of FIG. 1.

Referring to FIG. 2, pump 20 is seen to comprise a base 50 supporting a platen 52 which is biased upwardly therefrom by compressed springs 54. Couplings 56 and 58 are disposed on opposite ends of platen 52 and function to interconnect conduits 36 and 40 with the resilient pump tube 21, as shown. A similar arrangement is provided to interconnect conduits 38 and 42 with resilient pump tube 23, as shown in FIG. 1. Sprocket chains assemblies, indicated generally at 60 and 61, respectively, carry equally-spaced, rotatable pump rollers 62, 64, 66, 68, 70, 72, 74 and 76 extending therebetween. Each pump roller is operable, as shown for rollers 62, 64 and 66 in FIG. 2, to concurrently compress and occlude pump tubes 21 and 23 against the upper surface of platen 52. Drive means, indicated schematically at 78, are operable to drive the sprocket chain assemblies 60 and 61 in the indicated clockwise direction and at substantially constant speed. Accordingly, the pump rollers are, in turn, brought into contact with and progressively occlude the resilient pump tubes 21 and 23, with resultant pumping therethrough of successive samples and reagent, respectively, at substantially constant flow rates. The relative volumes of sample and reagent, i.e., proportioning, is determined by the relative internal diameters of pump tubes 21 and 23, respectively. Also, the pump rollers, in turn, release each of the pump tubes 21 and 23 which, as discussed hereafter, introduce a periodic pulsation into the otherwise constant flow rate along conduits 40 and 42. Pump 28 is of the same construction and manner of operation as pump 20 although, for purposes of this description, may be understood to comprise only four pump rollers 80, 82, 84 and 86 and a single resilient pump tube 45. A more complete understanding of the structure and operation of peristaltic pumps, such as pumps 20 and 28, may be had by reference to U.S. Pat. No. 2,865,303, assigned to a common assignee, and to U.S. Pat. No. 3,306,229, supra.

Figure 3:
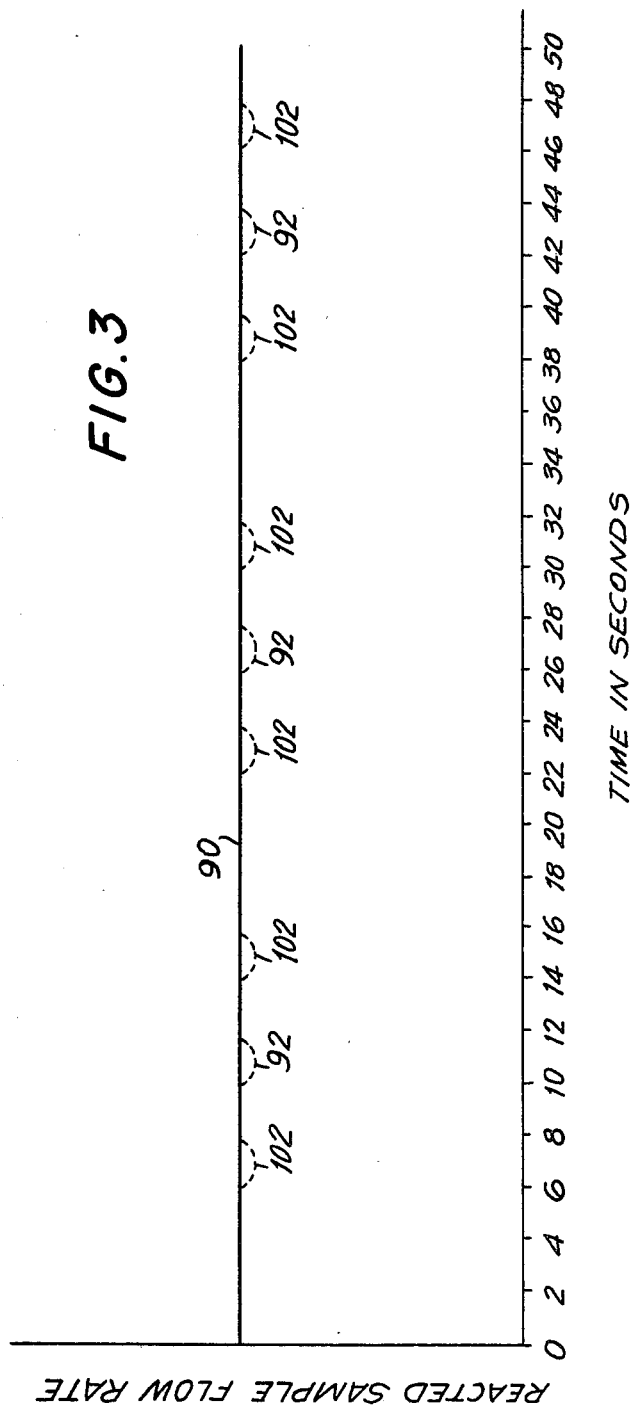
FIG. 3 is a graph illustrating the reacted sample flow rate.

Referring now to FIG. 3 of the drawings, and assuming proportioning pump 20 to be operating properly, the flow rate along resilient pump tubes 21 and 23 is substantially constant, except for periodic pulsations due to the lifting of the pump rollers, in turn, so as to provide a proper proportioning of sample and reagent and a substantially constant flow rate of reacted sample along mixing coil 24, as illustrated by curve 90. For purposes of discussion, the periodic pulsation resulting from the releasing of pump tubes 21 and 23 by the pump rollers are not illustrated. If a defect should exist in pump 20 causing, for example, less than full occlusion of either or both pump tubes 21 and 23 against platen 52 by any pump roller, e.g., 64, a pulsation in flow results in either or both of the sample and reagent flow rates, respectively, as indicated by the dashed line portions 92 of curve 90. In addition, any such defect in pump 20 will affect the proper proportioning of the sample and reagent passing along pump tubes 21 and 23, respectively. Such defect may be, for example, a flat spot on a roller, a failure of the roller to rotate properly, a defect in the sprocket chain assemblies 60 and 61, etc. Such pulsation 92 is periodic, occurring once during every operational cycle of pump 20. Thus, if it is assumed that pump 20 has an operational cycle time of sixteen seconds, i.e., the time required for a roller to be carried completely around by sprocket chain assemblies 60 and 61 and return to an initial position, such pulsation 92 occurs once every sixteen seconds and will reside in time generally at the same location within that sixteen-second interval. Also, assuming an operational cycle time of eight seconds for pump 28, any such defect, e.g. as in pump roller 86, will produce a pulsation 102 in the reacted sample flow rate which is repetitive each eight seconds, as hereafter discussed. Likewise, and although not shown, the pulsations due to releasing of the pump tubes 21 and 23, would be repetitive and perturb the flow rate each two seconds.

Figure 4:
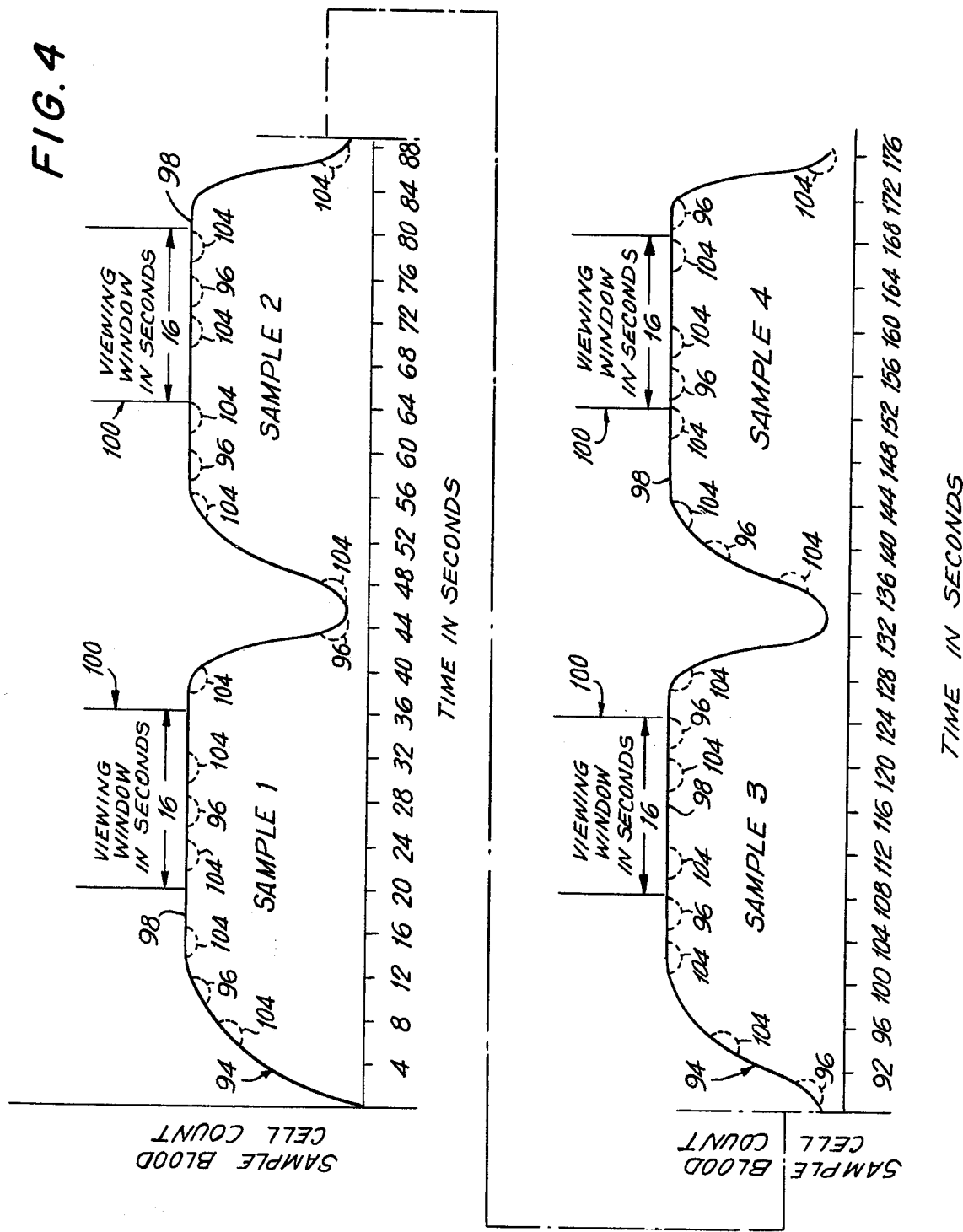
FIG. 4 is a graph illustrating the application of the method of the invention to the analysis results provided by the sample analysis apparatus of FIG. 1.

FIG. 4 depicts, in graphical form, the output curve 94 of flow cell 30, representing the results of cell counting of a number of successive samples, under constant flow rate conditions and with precise sample-reagent proportioning. Also, a same graphical form is applicable to "wet" chemistry systems, wherein the optical density of each successive reacted sample through flow cell 30 is measured to indicate the concentration of a particular analyte, as in U.S. Pat. No. 3,421,432, supra. Analysis apparatus 10 operates to count the total number of blood cells contained in a given quantity of reacted sample, which flows through flow cell 30 during a given time period, or "viewing" time. Hence, any pulsations in flow rate through flow cell 30 due to pump 28 adversely affects that flow cell output curve 94; also, and in respect of pump 20, any such pulsation will affect sample proportioning, as described. It will be appreciated that if pump 28 were not provided and pump 20 were the single pumping source, as is often done in continuous-flow analytical systems, any pulsations due to pump 20 would also affect flow rate through flow cell 30. In effect, pump 28 buffers flow cell 30 against pulsations in flow rate due to operation of pump 20 and, to some extent, against adverse effects on sample proportioning, as hereafter described. As will be appreciated by those skilled in the art, any such pulsations are somewhat muted during passage along apparatus 10. However, unless the conduit length of apparatus 10 is very considerable, such "muted" pulsations affect the output curve 94, as illustrated in FIG. 4.

More specifically, and if the output of mixing coil 24 were passed to debubbler 26 and directly to flow cell 30, as along conduit 44', indicated in dashed fashion and as conventionally done in certain types of "wet" chemistry systems, as illustrated in U.S. Pat. No. 3,241,432, supra, a pulsation 92 of approximately two-second duration will occur once during every sixteen-second operational cycle time of the "faulty" pump 20. Such pulsations 92 will affect sample proportioning and be reflected as decreases of like duration and like spacing in time in the flow rate along mixing coil 24, along conduit 44' and through flow cell 30.

FIG. 4 particularly illustrates that pulsations 96 or 104, resulting from pulsations 92 and 102, respectively, of FIG. 3, are substantially periodic and uniformly located or distributed along output curve 94 within the generally steady state portions 98 of curve 94 corresponding to each sample under analysis. For example, curve 94 in FIG. 4 illustrates the analytical results, whether from cell counting or optical density measurements, as indicated above, of four successive samples, i.e., "Sample 1", "Sample 2", "Sample 3", and "Sample 4", through flow cell 30. Only one pulsation 96 will occur in the steady-state 98 portion of Sample 1, while two pulsations 96 will occur in the steady-state portions 98 of each of Samples 2, 3, and 4. As indicated, distributions of pulsations 96 are periodic but will vary relative to the steady-state portions of the successive samples. The same is true with respect to pulsations 104 which are introduced by pump 28, if used. Also, it is evident that the periodic pulsations due to the release of pump tubes 21 and 23 by rollers of pump 20, if pump 28 is by-passed as by conduit 44', or of pump tube 45 by rollers of pump 20 would be distributed along output curve 94. Thus, pulsations 96 will affect the constancy of proportioning and constancy of flow rate, in the event that pump 28 is not utilized and the reacted sample is passed along conduit 44' to flow cell 30; pulsations 104 will affect only constancy of flow rate through flow cell 30. Accordingly, and in either event, pulsations due to the operation of pumps 20 and/or 28 affect the accuracy and reliability of the analysis results.

An analysis of this problem has revealed that, in accordance with the teachings of this invention, variations in sample proportioning and/or flow rate due to perturbations introduced by the inherent or faulty operation of pump structures can be compensated by particularly relating the duration of the "viewing window" 100 and the operational cycle time of pump structures employed in the apparatus. When a single pump is employed or several pumps of a same operation cycle time are employed, such relationship is fixed so that the duration of "viewing window" 100 and the operational cycle time are equal, or so that the latter is an integral sub-multiple of the former. When a plurality of pumps of different operational cycle times are employed, as with pumps 20 and 28, the relationship is further fixed such that the larger cycle time is an integral multiple of the shorter cycle time; alternatively, the shorter cycle time is an integral submultiple of the longer cycle time. When such relationship exists, accurate analytical results are assured, despite periodic variations in flow rate or sample proportioning introduced by the pumping structure(s), as described above. The analysis of the successive samples are effected under identical conditions and, hence, can be properly referenced to a standard, or calibration level, as conventionally done in continuous-flow analytical systems.

More specifically, and referring again to FIG. 4, signal detecting and processing means 32 (FIG. 1) is set to utilize a "viewing window" 100 of sixteen-second duration, which occurs within the steady-state portion 98 of curve 94 for each of the samples under analysis. Accordingly, and assuming that pump 28 is not used and pump 20 effects pumping directly through flow cell 30, one pulsation 96 occurs in the curve 94 within each "viewing window" 100 during which a sample is analyzed. Thus, sample-to-sample consistency of the analytical signals outputted by flow cell 30 and detected by signal detecting and processing means 32 is assured, despite variations in proportioning or apparatus flow rate introduced by a defect in pump 20. Conventionally, calibration is effected by reacting and analyzing a calibrant fluid of known characteristics in apparatus 10. The calibration results are used as a reference or standard against which the analytical results outputted by signal detecting and processing means 32 are compared.

Referring again to FIGS. 1 and 3, a defect in pump 28 results in less than full occlusion of resilient pump tube 45, so as to vary apparatus flow rate but, as described above, not proportioning. Pump 28 has an operational cycle time of eight-seconds, in accordance with the teachings of this invention (eight-seconds being an integral sub-multiple of the sixteen-second operational cycle of pump 20). Also, the operation of pump 28 may be synchronized with the operation of pump 20, whose operational cycle time is equal to the duration of "viewing window" 100. Accordingly, pulsations, indicated as 102 in FIG. 3 and generally of two-second duration, occur once during every eight-second time interval in curve 90 of FIG. 3. Pulsations 102 will, in the manner of pulsations 92, as described, reduce the flow rate through flow cell 30, as indicated in FIG. 3, and, correspondingly, the cell count level, as indicted in FIG. 4 by dashed line portions 104. Again, and since the eight-second operational cycle time of flow cell pump 28 is an integral sub-multiple of the sixteen-second time duration of the "viewing window" 100, a same number of reductions 104 occur within the "viewing window" 100 corresponding to each of the samples under analysis. Again, appropriate calibration of the apparatus 10 insures consistency and optimal accuracy of the overall analytical results.

Although described in detail hereinabove as applicable to compensate for variations in apparatus flow rate as caused by the faulty operation of pump 20 and/or pump 28, it is evident that the method of the invention is equally suited to situations wherein periodic reductions of the type illustrated as 96 and 104, are introduced into the output signal 94, as by periodic release of the pump tubes, as described.

Also, the method of this invention remedies the situation wherein the periodic defect in pump 20 results in less than full occlusion of one, rather than both, of pump tubes 21 and 23 by one of the pump rollers. Under such condtions, both the constancy of flow rate of the sample-reagent mixtures through the flow cell 30 and proper proportioning are again adversely affected. However, when pump 28 is not used, as discussed above, such mis-proportioning introduces periodic reductions of output curve 94 in the manner of reductions 96. Again, such "mis-proportioning" reductions are "viewed" once by the detecting means 32 during the sixteen-second "viewing window" 100 for each of the samples under analysis. Also, any periodic variations in proportioning, or reaction of the individual samples, are somewhat muted, as the sample stream through flow cell 30 has been debubbled. Further, when pump 28 is used, and inasmuch as the sample stream from coil 24 is debubbled and re-pumped by pump 28, any inconsistency in proportioning is further muted by flowing through pump 28. However, if the flow output of coil 24 is passed directly to flow cell 30, as often done in systems of the type illustrated, it will be appreciated that any variations in proportioning and, also, flow rate due to faulty operation of pump 20 would be compensated, as described.

It should be clear that the method of the invention would be equally applicable to a wide variety of other and different apparatuses and systems, wherein periodic and undesired pulsations are introduced into a flowing fluid stream. Also, the method of the invention applies to systems for performing, for example, automated hemaglobin determinations, wherein the analytical measurements are integrated for a period of time commensurate with the time duration of the "viewing window". Also, there is, of course, no requirement for satisfactory utilization of the method of this invention that the samples under analysis be blood. It will be appreciated that such method is equally applicable to apparatus as may include a greater or lesser number of pumps as long as the relationship between the detecting time and the operational cycle time(s) of the included pump(s) are fixed, as described, and also to multi-channel analysis apparatus of the nature disclosed, for example, in U.S. Pat. No. 3,241,432, wherein a plurality of different analyses are simultaneously conducted on each of a series of samples in succession. In the latter event, the respective "viewing windows" of the individual analytical channels would, in each instance, be related, as described, to the operational cycle time(s) of the pump(s) included in the individual channel.

Further, and although disclosed by way of example hereinabove as applied to circumstances wherein the defect(s) in the pump(s) result in periodic decreases in the level of flow cell output curve 94, it will be readily understood by those skilled in this art that the teachings of the method of the invention would be equally applicable to circumstances wherein such defect(s) result in periodic increases in the level of that flow cell output curve.

Various changes may, of course, be made in the hereindisclosed embodiment of this invention without departing from the spirit and scope thereof as defined in the appended claims.

What is claimed is:

1. A method of treating a flowing stream wherein perturbations in flow and/or composition are periodically introduced, said perturbations having a fixed frequency, comprising the steps of:
   (a) flowing said fluid stream along a conduit; and
   (b) repeatedly treating said flowing stream in fixed relationship to the periodicity of said perturbations, so as to overcome the effects of said perturbations.

2. The method as in claim 1, wherein the step of flowing said stream includes the further steps of introducing successive and discrete liquid segments along said conduit and reacting said liquid segments, and said treating step includes detecting the product of said reaction step.

3. The method as in claim 1, wherein the step of flowing said stream includes peristaltically pumping said stream, said perturbations being introduced during said pumping step.

4. The method of claim 2, wherein said treating step has a time duration equal to the period of said perturbations.

5. The method of claim 4, wherein said treating step has a time duration which is an integral multiple of the period of said perturbations.

6. In a method for determining the results of the operation of continuous flow fluid sample analysis apparatus which are operable to successively mix a plurality of samples with a reagent in predetermined proportion and to successively analyze the thusly reacted samples, said apparatus comprising pump means having a predetermined operational cycle time and which are operable to concomitantly pump the fluid samples in succession, and the reagent in predetermined proportion thereto, through said apparatus at substantially constant flow rate for analysis based on the sample-reagent reaction for each of said samples, and detecting means which are operable to detect the analysis results in succession for a predetermined detecting time for each of said reacted samples, the improvements comprising, the steps of, fixing the relationship between said operational cycle time and said detecting time in such manner that variations in apparatus flow rate and/or sample-reagent proportioning occuring periodically during each operational cycle of said pump will affect the analysis results for each of said samples in like manner whereby, the sample-to-sample consistency of said analysis results is maintained despite said variations.

7. In a method as in claim 6 wherein, said relationship is fixed so that said detecting time and said operational cycle time are equal.

8. In a method as in claim 6 wherein, said relationship is fixed so that said operational cycle time is an integral sub-multiple of said detecting time.

9. In a method as in claim 6 wherein, said sample analysis apparatus comprises a plurality of pump means, at least two of which have different predetermined operational cycle times, and wherein the relationships between said detecting time and said different operational cycle times are fixed so that one of said operational cycle times is equal to said detecting time, and the other of said operational cycle times is an integral sub-multiple of said detecting time.

10. In a method as in claim 6 wherein, said sample analysis apparatus comprises additional pump means downstream in said apparatus of said first-mentioned pump means, said additional pump means being operable to pump the reacted samples through said analysis apparatus, said additional pump means having a different operational cycle time than said first-mentioned pump means, and wherein the method further comprises, the steps of, fixing the relationship between said detecting time and said different operational cycle times so that one of said operational cycle times is equal to said detecting time, and the other of said operational cycle times is an integral sub-multiple of said detecting time.

11. In a method as in claim 10 wherein, said relationship is fixed so that the operational cycle time of said first-mentioned pump means is made equal to said detecting time, and the operational cycle time of said additional pump means is an integral sub-multiple of said detecting time.

* * * * *